US006695833B1

(12) United States Patent
Frantzen (10) Patent No.: US 6,695,833 B1
(45) Date of Patent: Feb. 24, 2004

(54) VASCULAR STENT-GRAFT APPARATUS AND FORMING METHOD

(75) Inventor: John J Frantzen, Laguna Niguel, CA (US)

(73) Assignee: Nellix, Inc., S. San Francisco, CA (US)

( * ) Notice: Subject to any disclaimer, the term of this patent is extended or adjusted under 35 U.S.C. 154(b) by 219 days.

(21) Appl. No.: 09/671,550

(22) Filed: Sep. 27, 2000

(51) Int. Cl.$^7$ ................................................ A61F 2/06
(52) U.S. Cl. ..................................... 606/1.13; 623/901
(58) Field of Search ............................. 623/901, 1.13, 623/1.44, 1.35, 1.46; 606/191, 195, 198

(56) References Cited

U.S. PATENT DOCUMENTS

| | | | |
|---|---|---|---|
| 4,704,126 A | 11/1987 | Baswell | |
| 4,710,192 A | 12/1987 | Liotta | |
| 4,743,258 A | 5/1988 | Ikada | |
| 4,856,516 A | 8/1989 | Hillstead | |
| 4,858,264 A | 8/1989 | Reinhart | |
| 4,892,544 A | * 1/1990 | Frisch | ........................ 623/901 |

(List continued on next page.)

FOREIGN PATENT DOCUMENTS

EP 95302708.3 4/1995

OTHER PUBLICATIONS

Patrick W. Serruys and Michael JB Kutryk, Handbook of Coronary Stents, 1998, pp. 45, 55, 78, 103, 112, 132, 158, 174, 185, 190, 207, 215, 230, 239, Second Edition, Martin Dunitz, United Kingdom.

Journal of Endovascular Therapy, Apr. 2000, pp. 111, 114, 132–140, vol. 7, No. 2, International Society of Endovascular Specialists, Phoenix, AZ.

Primary Examiner—Kevin T. Truong
(74) Attorney, Agent, or Firm—Heisler & Associates (57) ABSTRACT

A stent-graft is provided which includes a smooth continuous inside surface for efficient fluid flow therethrough. The stent-graft can be implanted intraluminally by radially expanding the stent-graft adjacent an area within the body lumen to be treated, or can be implanted utilizing direct surgical techniques. A cylindrical support structure is preferably provided which is at least partially embedded along with portions of the film. The cylindrical support structure can facilitate radial expansion and provide additional structural strength to the stent-graft. A woven fabric support structure can also be embedded within the film of solid material forming the stent-graft to provide additional support to the stent-graft and allow suturing of the stent-graft to walls of the body lumen. Various different geometric configurations can be provided for the stent-graft. To form the stent-graft a mandrel is placed within a vacuum and a film of material, such as parylene, is deposited upon the mandrel. Additional layers of parylene film can be deposited to embed at least portions of the cylindrical support structure and/or the woven fabric support structure within the film of parylene forming the stent-graft. A coupling system including a collar with a circumferential groove can similarly be embedded within the stent-graft by deposition of additional layers of parylene film. Separate bands can reside within the groove partially and hold a portion of the wall of the lumen between the band and the groove of the collar to secure an end of the stent-graft adjacent the lumen.

11 Claims, 5 Drawing Sheets

U.S. PATENT DOCUMENTS

| | | |
|---|---|---|
| 4,936,057 A | 6/1990 | Rhoades |
| 4,976,692 A | 12/1990 | Atad |
| 5,002,532 A | 3/1991 | Gaiser |
| 5,074,845 A | 12/1991 | Miraki |
| 5,104,404 A | 4/1992 | Wolff |
| 5,108,417 A | 4/1992 | Sawyer |
| 5,133,732 A | 7/1992 | Wiktor |
| 5,139,480 A | 8/1992 | Hickle |
| 5,195,984 A | 3/1993 | Schatz |
| 5,199,226 A | 4/1993 | Rose |
| 5,217,484 A | 6/1993 | Marks |
| 5,234,437 A | 8/1993 | Sepetka |
| 5,242,399 A | 9/1993 | Lau |
| 5,250,071 A | 10/1993 | Palermo |
| 5,261,916 A | 11/1993 | Engelson |
| 5,263,964 A | 11/1993 | Purdy |
| 5,314,444 A | 5/1994 | Gianturco |
| 5,334,217 A | 8/1994 | Das |
| 5,350,397 A | 9/1994 | Palermo |
| 5,352,199 A | 10/1994 | Tower |
| 5,375,612 A | 12/1994 | Cottenceau |
| 5,383,892 A | 1/1995 | Cardon |
| 5,421,955 A | 6/1995 | Lau |
| 5,423,849 A | 6/1995 | Engelson |
| 5,425,739 A | 6/1995 | Jessen |
| 5,425,744 A | 6/1995 | Fagan |
| 5,441,510 A | 8/1995 | Simpson |
| 5,441,515 A | 8/1995 | Khosravi |
| 5,443,477 A | 8/1995 | Marin |
| 5,443,496 A | 8/1995 | Schwartz |
| 5,449,373 A | 9/1995 | Pinchasik |
| 5,485,667 A | 1/1996 | Kleshinski |
| 5,494,029 A | 2/1996 | Lane |
| 5,496,277 A | 3/1996 | Termin |
| 5,507,767 A | 4/1996 | Maeda |
| 5,507,771 A | 4/1996 | Gianturco |
| 5,514,115 A | 5/1996 | Frantzen |
| 5,514,154 A | 5/1996 | Lau |
| 5,522,882 A | 6/1996 | Gaterud |
| 5,531,741 A | 7/1996 | Barbacci |
| 5,545,210 A | 8/1996 | Hess |
| 5,549,662 A | 8/1996 | Fordenbacher |
| 5,549,663 A | 8/1996 | Cottone |
| 5,554,181 A | 9/1996 | Das |
| 5,562,641 A | 10/1996 | Flomenblit |
| 5,562,698 A | 10/1996 | Parker |
| 5,562,728 A | 10/1996 | Lazarus |
| 5,569,295 A | 10/1996 | Lam |
| 5,578,074 A | 11/1996 | Mirigian |
| 5,578,149 A | 11/1996 | De Scheerder |
| 5,591,195 A | 1/1997 | Taheri |
| 5,591,197 A | 1/1997 | Orth |
| 5,591,223 A | 1/1997 | Lock |
| 5,591,226 A | 1/1997 | Trerotola |
| 5,591,230 A | 1/1997 | Horn |
| 5,601,600 A | 2/1997 | Ton |
| 5,603,721 A | 2/1997 | Lau |
| 5,605,530 A | 2/1997 | Fischell |
| 5,607,442 A | 3/1997 | Fischell |
| 5,607,445 A | 3/1997 | Summers |
| 5,609,605 A | 3/1997 | Marshall |
| 5,618,299 A | 4/1997 | Khosravi |
| 5,624,411 A | 4/1997 | Tuch |
| 5,630,840 A | 5/1997 | Mayer |
| 5,632,760 A | 5/1997 | Sheiban |
| 5,632,763 A | 5/1997 | Glastra |
| 5,632,771 A | 5/1997 | Boatman |
| D380,266 S | 6/1997 | Boatman |
| 5,634,941 A | 6/1997 | Winston |
| 5,636,641 A | 6/1997 | Fariabi |
| D380,831 S | 7/1997 | Kavteladze |
| 5,674,241 A * | 10/1997 | Bley et al. .................. 623/1.2 |
| 5,683,449 A | 11/1997 | Marcade |
| 5,690,643 A | 11/1997 | Wijay |
| 5,693,067 A | 12/1997 | Purdy |
| 5,697,971 A | 12/1997 | Fischell |
| 5,709,707 A | 1/1998 | Lock |
| 5,718,713 A | 2/1998 | Frantzen |
| 5,723,004 A * | 3/1998 | Dereume et al. .......... 623/1.35 |
| 5,725,572 A | 3/1998 | Lam |
| 5,728,068 A | 3/1998 | Leone |
| 5,728,158 A | 3/1998 | Lau |
| 5,735,892 A * | 4/1998 | Myers et al. .............. 623/1.13 |
| 5,735,893 A | 4/1998 | Lau |
| 5,741,327 A | 4/1998 | Frantzen |
| 5,741,333 A | 4/1998 | Frid |
| 5,746,691 A | 5/1998 | Frantzen |
| 5,755,769 A | 5/1998 | Richard |
| 5,755,778 A | 5/1998 | Kleshinski |
| 5,766,238 A | 6/1998 | Lau |
| 5,776,114 A | 7/1998 | Frantzen |
| 5,776,154 A | 7/1998 | Taylor |
| 5,776,161 A | 7/1998 | Globerman |
| 5,782,907 A | 7/1998 | Frantzen |
| 5,788,626 A * | 8/1998 | Thompson ................. 623/1.44 |
| 5,797,953 A | 8/1998 | Tekulve |
| 5,800,393 A | 9/1998 | Sahota |
| 5,800,514 A | 9/1998 | Nunez |
| 5,800,525 A | 9/1998 | Bachinski |
| 5,807,404 A | 9/1998 | Richter |
| 5,810,872 A | 9/1998 | Kanesaka |
| 5,824,036 A | 10/1998 | Lauterjung |
| 5,824,040 A | 10/1998 | Cox |
| 5,824,049 A * | 10/1998 | Ragheb et al. ............. 623/1.44 |
| 5,824,056 A | 10/1998 | Rosenberg |
| 5,827,321 A | 10/1998 | Roubin |
| 5,836,966 A | 11/1998 | St. Germain |
| 5,843,175 A | 12/1998 | Frantzen |
| 5,846,246 A | 12/1998 | Dirks |
| 5,849,037 A | 12/1998 | Frid |
| 5,863,627 A | 1/1999 | Szycher |
| 5,868,708 A | 2/1999 | Hart |
| 5,868,782 A | 2/1999 | Frantzen |
| 5,873,907 A | 2/1999 | Frantzen |
| 5,879,381 A | 3/1999 | Moriuchi |
| 5,894,843 A | 4/1999 | Benetti |
| 5,902,332 A | 5/1999 | Schatz |
| 5,919,224 A | 7/1999 | Thompson |
| 5,931,866 A | 8/1999 | Frantzen |
| 5,947,991 A | 9/1999 | Cowan |
| 5,948,184 A | 9/1999 | Frantzen |
| 5,984,955 A | 11/1999 | Wisselink |
| 6,007,573 A | 12/1999 | Wallace |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,123,722 A * | 9/2000 | Fogarty et al. .............. 623/1.1 |
| 6,152,144 A | 11/2000 | Lesh |
| 6,187,033 B1 | 2/2001 | Schmitt |
| 6,203,732 B1 * | 3/2001 | Clubb et al. ................ 623/901 |
| 6,241,761 B1 * | 6/2001 | Villafana .................. 623/1.13 |
| 6,299,604 B1 | 10/2001 | Ragheb |
| 6,325,816 B1 | 12/2001 | Fulton |
| 6,334,868 B1 | 1/2002 | Ham |
| 6,451,047 B2 * | 9/2002 | McCrea et al. ............ 623/1.13 |

* cited by examiner

VASCULAR STENT-GRAFT APPARATUS AND FORMING METHOD

FIELD OF THE INVENTION

The following invention relates to stent-grafts which are utilized to support or replace a damaged body lumen, such as an artery. More particularly, this invention relates to vascular stent-grafts which can be implanted intraluminally or with direct surgical techniques and which provide a smooth continuous elongate tube structure for transport of bodily fluids through the damaged area.

BACKGROUND OF THE INVENTION

Body lumens such as arteries can become damaged in a variety of different ways. For instance, diseases such as arteriosclerosis and aneurysms result in degeneration of the arterial wall. Depending on the type of damage to the artery and the extent of such damage, various different treatments can be used for these conditions. Where the damaged artery wall is still somewhat viable, a radially expandable stent can be implanted intraluminally and radially expanded at the site of damage to support the wall in the desired open position. Examples of such stents can be found in the Handbook of Coronary Stents, Second Edition. Stent-grafts are also described in journals such as the Journal of Endovascular Therapy (see for example issue 2000; 7) U.S. Pat. No. 6,042,606, incorporated herein by reference, also describes details of surgical stents utilizable to support a damaged artery wall or other body lumen.

When the artery wall is sufficiently deteriorated that it can no longer function properly, a graft can be placed within the damaged portion of the artery to support blood flow or other body fluid flow past the damaged area. While such grafts include a structural component to keep the graft in a desired location and/or shape, they are referred to as stent-grafts. Such stent-grafts can come in two varieties. First, the stent-graft can be placed intraluminally within the damaged portion of the artery with the damaged portion of the artery remaining in position but no longer being relied upon to support blood flow past the damaged area. Second, the stent-graft can directly be surgically implanted by removal of the damaged artery section and replacement with the stent-graft.

Such stent-grafts provide a number of basic functions. They include a solid film which is impervious to fluid flow therethrough so that it can contain blood or other bodily fluid flow within the lumen pathway. They include some structure for securely holding the stent-graft in position adjacent the damaged portion of the artery and to keep a desired shape for the stent-graft and exhibit sufficient structural strength to handle the fluid pressure and surrounding forces without failure.

Known prior art stent-grafts have included a separate fluid containment layer and a separate structural support layer. For instance, the World Medical Manufacturing Corporation of Sunrise, Fla. produces a stent-graft under the trademark TALENT that includes a Dacron fabric covering a radially expandable nickel-titanium support structure (see the Journal of Endovascular Therapy 2000; 7: 132–135, 133). Other known stent-grafts include the JOSTENT peripheral stent-graft manufactured by Jomed International AB, Stockholm, Sweden which includes a polytetrafluoroethylene covering internal to the structural portions of the stent-graft (see Journal of Endovascular Therapy 2000; 7: 136–140, 138).

While such known prior art stent-grafts are generally effective, they suffer from certain drawbacks. They are not all formed in a manner which provides a continuous layer of material. Rather, the covering is typically a woven fabric which can be susceptible to leakage, especially adjacent where sutures are utilized to hold the stent-graft in place. Additionally, they generally suffer from poor integration of the covering layer with the support structure, resulting in locations for restenosis and other corrosive material within the stent-graft which can lead to fluid disruption through the stent-graft.

They also are difficult to collapse and expand radially to a great extent. Accordingly, a need exists for a stent-graft which provides a smooth continuous inside surface and which can readily be positioned either intraluminally or with direct surgery at a site where a body lumen is damaged.

SUMMARY OF THE INVENTION

This invention provides a stent-graft which includes a smooth solid film providing an inside surface which is free of irregularities in texture and which is non-foraminous, rather than formed from a woven material with the intended gaps between threads or other porous material. This film can provide the tubular structure of the stent-graft alone or can be supported with various different support structures. The support structures can be metallic, such as a radially expandable stent structure or can be a woven support structure. In either case, the support structure is at least partially embedded within the film so that surface irregularities are not introduced by the inclusion of the support structure. The stent-graft can be a tubular structure with two ends or can have intersections therein so that multiple different arms of the tubular structure of the stent-graft can be joined together and can be utilized to treat body lumens which have junctions therein.

Ends of the stent-graft can be attached to adjacent body lumens in one or more of three main ways. First, the stent-graft can be radially expanded and be formed from a shape memory material which exerts sufficient outward radial pressure against the lumen wall to hold the stent-graft in place. Second, sutures or other surgical structure attachment structures, such as clips, staples and the like, can be utilized directly between the stent-graft structure adjacent the ends and the lumen wall adjacent the stent-graft. Third, a band and collar combination can be utilized where a collar is included near an end of the stent-graft which has a groove passing circumferentially around the collar and with a band which can mate with the collar and extend into the groove somewhat with the lumen wall between the band and the groove, so that the collar and band together form a coupling to securely hold the stent-graft to the lumen.

While various different materials can form the film and other portions of the stent-graft, a parylene material is preferred. Parylene can be deposited within a vacuum onto a mandrel having a shape similar to the interior surface of the stent-graft. Hence, the stent-graft can be formed merely by depositing the parylene material onto the mandrel and then later removal of the mandrel, such as by chemically dissolving the mandrel. Additional layers of parylene or other coatings can later be applied to the stent-graft to bond at least portions of a support structure to the stent-graft. The support structure provides radial expandability, enhanced strength and resistance to tearing for the stent-graft and is incorporated directly into the film of the stent-graft.

OBJECTS OF THE INVENTION

Accordingly, a primary object of the present invention is to provide a stent-graft which provides a smooth, continuous, non-foraminous inside surface which can be utilized to be surgically implanted adjacent a damaged lumen to support fluid flow through the lumen.

Another object of the present invention is to provide a stent-graft which can be implanted intraluminally and then be radially expanded at the desired location to support fluid flow at the desired location.

Another object of the present invention is to provide a stent-graft which can be implanted with direct surgical techniques to replace a damaged body lumen.

Another object of the present invention is to provide a stent-graft which includes both a film and a support structure embedded within the film but formed from a different material with at least inside surfaces of the support layer remaining smooth and with secure coupling of the support structure with the film.

Another object of the present invention is to provide a coupling system for coupling stent-grafts to body lumens in a secure fashion.

Another object of the present invention is to provide a stent-graft which can be implanted and held in place with sutures without risk of tearing of the stent-graft.

Another object of the present invention is to provide a stent-graft which is formed from bio-compatible materials.

Another object of the present invention is to provide a stent-graft which includes multiple different arms for use in treating a branch in a body lumen which is damaged.

Another object of the present invention is to provide a method for manufacturing a stent-graft which avoids any need for seams which provides a smooth inside surface and secure coupling of a support layer of the stent-graft with support structure within the stent-graft.

Other further objects of the present invention will become apparent from a careful reading of the included drawing figures, the claims and detailed description of the invention.

DESCRIPTION OF THE PREFERRED EMBODIMENT

Referring to the drawings, wherein like, reference numerals represent like parts throughout the various drawing figures, reference numeral 10 is directed to a preferred radially expandable stent-graft of this invention. The stent-graft 10 can be implanted intraluminally and then radially expanded, along arrow R, away from a central axis 2 to support the body lumen L and route fluid passing through the body lumen L along the central axis Z, along arrow A (FIG. 1) through the stent-graft 10.

Figures 1, 2, 3:
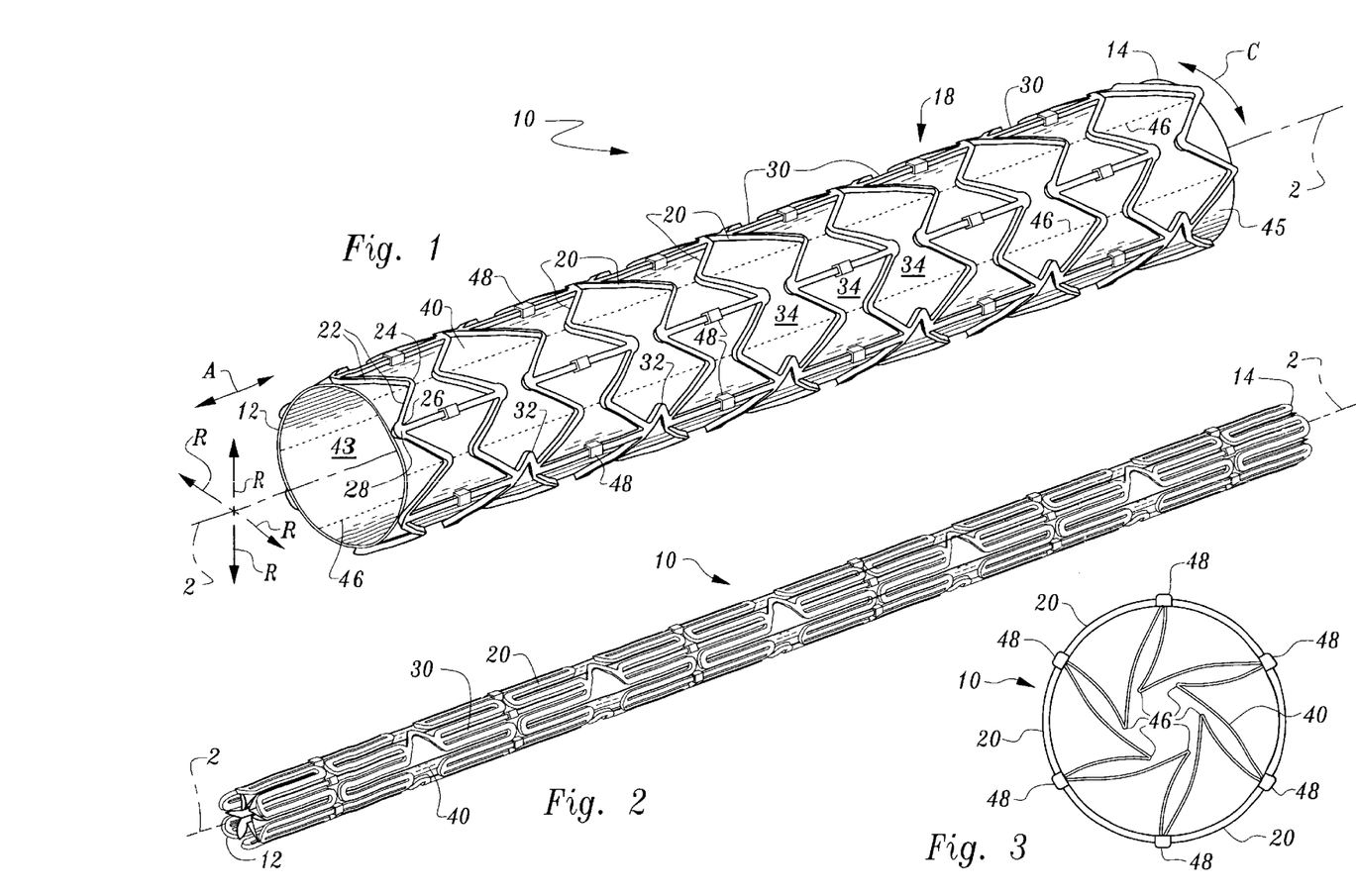
FIG. 1 is a perspective view of a preferred embodiment of the stent-graft of this invention which includes a cylindrical support structure and a film providing an inside surface of the stent-graft and with the film selectively attached to the cylindrical support structure at selective locations where movement between the film and the cylindrical support structure is not required during radial expansion of the cylindrical support structure.
FIG. 2 is a perspective view of that which is shown in FIG. 1 before radial expansion.
FIG. 3 is an end view of that which is shown in FIG. 2 illustrating how the film can fold when the cylindrical support structure is collapsed.

In essence, and with particular reference to FIGS. 1–3, details of the stent-graft 10 of the preferred embodiment are described. The stent-graft 10 is preferably radially symmetrical and substantially cylindrical in construction about the central axis 2. The stent-graft 10 is a generally tubular structure which extends from a first end 12 to a second end 14. The stent-graft 10 includes two primary portions including a cylindrical support structure 18 which provides enhanced structural strength and assists in causing radial expansion of the stent-graft 10, and a film 40 which provides the conduit for support of fluid flow through the stent-graft 10.

The cylindrical support structure 18 and film 40 are preferably integrated together somewhat as described in detail below. The cylindrical support structure 18 includes circumferential elements 20 which extend circumferentially, along arrow C, about the central axis 2. Axial elements 30 join the separate circumferential elements 20 together. Axial links 32 also join some of the circumferential elements 20 together. The circumferential elements 20, axial elements 30 and axial links 32 together form the cylindrical support structure 18. The support structure 18 can transition between a radially collapsed form (FIG. 2) to a radially expanded form (FIG. 1) by expansion of the cylindrical support structure 18 along arrow R (FIG. 1).

The support layer 40 preferably includes an inside layer 42 (FIG. 5) and an outside layer 44 with portions of the cylindrical support structure 18 surrounded by the layers 42, 44 of the film 40. An inside surface 43 is very smooth and free of surface irregularities which could disrupt fluid flow and provide sites for restenosis or other disruptive conditions. Fold lines 46 in the film 40 define locations where the film 40 can be folded when the stent-graft 10 is radially collapsed (FIG. 2). The fold lines 46 can be provided strategically so that a proper collapsing pattern can be provided (FIG. 3). More specifically, and with particular reference to FIGS. 1–3, the specific details of the stent-graft 10 are described. The cylindrical support structure 18 preferably includes the circumferential elements 20 including linear segments 22 spaced from each other by alternating crests 24 and troughs 26. Junctions 28 define locations on the circumferential elements 20 where axial elements 30 or axial links 32 are joined to the circumferential elements 20. Gaps 34 are located between adjacent circumferential elements 20.

Each gap 34 is spanned by either an axial element 30 or an axial link 32. The axial elements 30 are preferably linear and extend between troughs 26 of adjacent circumferential elements 20. The axial links 32 preferably have a bent configuration and extend between crests 24 of adjacent circumferential elements 20. Each bend in the circumferential elements 20 can be either a crest 24 or a trough 26 depending on which side of the circumferential element 20 is being referred to. Preferably, each gap 34 is only spanned by either axial elements 30 or axial links 32, and not a combination of axial elements 30 and axial links 32. In this way, gaps 34 spanned by axial elements 30 are generally widened when the stent-graft. 10 is radially expanded and the gaps 34 spanned with axial links 32 are generally narrowed as the stent-graft 10 is radially expanded.

While the above described cylindrical support structure 18 for the stent-graft 10 is preferred, various different segment and junction, configurations could similarly be utilized. For instance, a single segment can extend helically to form a cylindrical support structure. A full discussion of various stent segment patterns is provided in Handbook of Coronary Stents, Second Edition. Any of the prior art stents disclosed in that reference or otherwise known in the prior art which exhibit radial expandability could conceivably be adapted for use within the stent-graft 10 as the cylindrical support structure 18.

When the cylindrical support structure 18 is radially expanding, it can readily be determined by observation that some portions of the cylindrical support structure 18 pivot and otherwise move in a manner other than radially during radial expansion. If the film 40 is formed of a non-elastic material, these portions of the cylindrical support structure 18 which pivot and otherwise move in a non-radial direction to allow the stent-graft 10 in expanding radially, have a potential for tearing the film 40 or restricting radial expansion of the stent-graft 10.

Preferably, the cylindrical support structure 18 is formed in a manner so that certain portions of the cylindrical support structure 18 only move radially during radial expansion of the stent-graft 10. For instance, in FIG. 1 the axial elements 30 and the axial links 32 remain substantially stationary, except for radial translation (along arrow R of FIG. 1) during radial expansion of the stent-graft 10. However, the linear segments 22 and crests 24 and troughs 26 which are spaced from junctions 28 do move in an at least partially axial manner during radial expansion of the stent-graft 10.

Preferably, these portions of the cylindrical support structure 18 which move in a manner other than radially are not directly connected to the film 40. Rather, attachments 48 are preferably provided between the film 40 and the axial elements 30, axial links 32 or other portions of the cylindrical support structure 18 which only move radially. In this way, the cylindrical support structure 18 can be securely attached to the film 40 but the film 40 does not in any way restrict radial expansion of the cylindrical support structure 18 of the stent-graft 10. While the attachments 48 are shown adjacent each axial element 30, the attachments 48 could be provided on less than all of the axial elements 30, such as with attachments 48 included adjacent two of the six axial elements within each gap 34.

Preferably, the cylindrical support structure 18 is similar to that provided in U.S. Pat. No. 6,042,606 incorporated herein by reference. As disclosed in this other patent, the various portions of the cylindrical support structure 18 would be formed from a nickel-titanium shape memory material which would be biased towards the radially expanded configuration so that the cylindrical support structure 18 and hence the entire stent-graft 10 would be somewhat self-expanding once implanted. Additionally, couplings, sutures or other attachment techniques can be utilized to secure the stent-graft 10 in its radially expanded form and to securely attach the stent-graft 10 to adjacent walls W of the lumen L. Alternatively, the cylindrical support structure 18 can be formed of stainless steel or other non-shape memory materials and a balloon can be utilized to expand the stent-graft 10.

Figure 5:
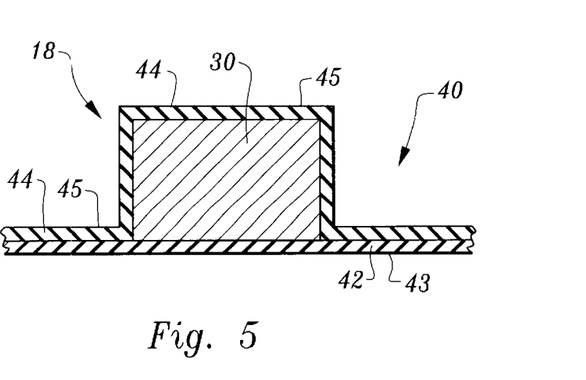
FIG. 5 is a sectional view taken along line 5—5 of FIG. 6 illustrating how the film of the stent-graft can totally surround the cylindrical support structure or other support structure of the stent.

With particular reference to FIG. 5, details of the film 40 and the method of manufacturing the stent-graft 10 are described. Preferably, the film 40 includes two separate layers including an inside layer 42 and an outside layer 44. An inside surface 43 of the film 40 is provided by the inside layer 42. An outside surface 45 of the film 40 is provided by the outside layer 44. Preferably, the cylindrical support structure 18 is generally adjacent the outside surface 45 of the outside layer 44. However, it is most preferable that at least portions of the cylindrical support structure 18 be embedded within the film 40.

Specifically, the outside layer 44 can go over one side of the cylindrical support structure 18 and the inside layer 42 can pass over an opposite side of the cylindrical support structure 18, so that the cylindrical support structure 18 is in fact sandwiched between the inside layer 42 and the outside layer 44 of the film 40. As discussed above, such sandwiching of the cylindrical support structure 18 can be limited to attachments 48 at locations on the stent-graft 10 where pure radial translation occurs, so that distortion of the film 40, damage to the film 40 or restriction and radial expansion of the stent-graft 10 are avoided.

Alternatively, the film 40 can be formed from a sufficiently flexible material that elasticity within the film 40 can accommodate the motion of various portions of the cylindrical support structure 18 during radial expansion of the stent-graft 10. Where the film 40 is sufficiently elastic, the implanted stent 50 of the FIG. 4 or the flat edge stent 60 of FIG. 6 can effectively be utilized.

The film 40 is preferably formed from a parylene film which is between 0.0001 and 0.002 inches thick, with 0.0005 inches considered an ideal thickness. Parylene is the generic name for members of a family of polymeric di-parazylylenes. Parylene refers to such thermoplastic polymers that can be formed on surfaces exposed to a rarefied gas in a vacuum. To create the film 40, the parylene can be deposited onto a mandrel or other deposition surface laying adjacent where the film 40 is to be formed during the vacuum deposition process. Alternatively, a thin flexible base layer can be located where the film 40 is to be formed and then the parylene can be deposited directly onto this base layer to create the parylene layer forming the film 40. If desired, the entire stent-graft 10, including the cylindrical support structure 18, can be coated with the parylene that forms the film 40.

As an alternative, the film 40 can be formed as a silicone film or from high strength copolymers of silicone and a polycarbonate, such as products marketed under the trademark CHRONOFLEX manufactured by Cardiotech International of Woburn, Mass. While not preferred, other appropriate materials, such as polyesters or polytetrafluoroethylene or any other appropriate flexible surface materials, can be utilized to create the film 40.

Most preferably, the film 40 is formed as a parylene film following a vacuum deposition process as follows. Initially, a mandrel is provided having external geometric features matching those desired for the inside surface 43 of the inside layer 42 of the stent-graft 10. This mandrel is placed within the vacuum chamber and the parylene layer of desired thickness is deposited onto the mandrel. The inside layer 42 has thus been formed. The cylindrical support structure 18 is then placed over the inside layer 42. A masking agent is then optionally placed over the cylindrical support structure 18 at locations on the cylindrical support structure 18 where it is desired that no portion of the outside layer 44 be provided.

The mandrel, inside layer 42 and cylindrical support structure 18 then have the outside layer 44 of parylene deposited onto the unmasked portions of the inside layer 42 and the cylindrical support structure 18. Finally, the masking agent is removed with the stent-graft 10 having portions of the cylindrical support structure 18 embedded within the film 40 provided (FIG. 1).

If desired, perforations or areas of decreased thickness can be provided within the film 40 along the fold line 46. When the stent-graft 10 is radially collapsed (FIG. 2) the film 40 is encouraged to extend inward and fold in a predictable pattern, such as that shown in FIG. 3. The cylindrical support structure 18 and the film 40 together define the tube structure of the stent-graft according to this preferred embodiment. The film 40 is solid and non-foraminous so that no holes pass through the film 40, as would be the case with woven fabric tubular structures. Also, the film is free of any surface irregularities and is smooth, unlike fabrics which have a texture of varying roughness that would provide a greater resistance to fluid flow then the smooth parylene film 40.

A sheath can be provided over an exterior of the stent-graft 10 to restrain the stent-graft 10 in its radially collapsed configuration. The stent-graft 10 can then be placed upon a catheter and navigated intraluminally to the desired implantation site. The sheath is then removed from the exterior of the stent-graft 10 and the stent-graft 10 is allowed to expand radially to its final configuration (FIG. 1). If necessary, a radially expandable balloon can be utilized to encourage and ensure that the stent-graft 10 has fully radially expanded. Due to the shape memory of the cylindrical support structure 18 within the stent-graft 10, the stent-graft 10 can be slightly oversized for the body lumen L and hence exert a radial outward pressure on the body lumen L and tend to hold itself in place without requiring additional attachment structures. If necessary, sutures can be utilized passing through the film 40 and the wall W of the lumen L (i.e. FIG. 15) to hold the stent-graft 10 in position.

Where direct surgical implantation is to be provided, the surgical site is accessed through a main incision and the damaged portion of the body lumen L is typically removed. Ends 12, 14 of the stent-graft 10 are then attached to the healthy ends of the wall W of the lumen L, as described above and shown in FIG. 15, to secure the stent-graft 10 in position as desired. Once implanted, the stent-graft 10 handles flow of fluid through an interior of the stent-graft 10, along the central axis 2, effectively bypassing the damaged portion of the lumen L.

Figure 4:
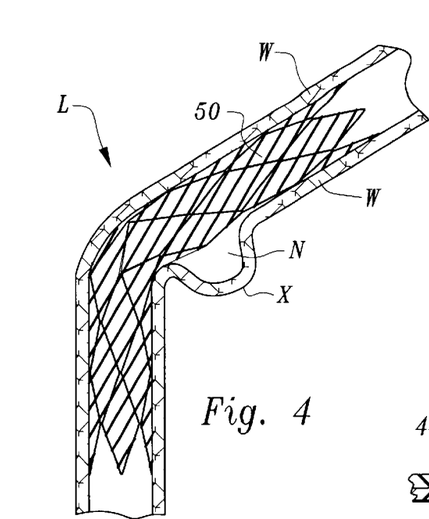
FIG. 4 is a sectional view of a body lumen with a stent-graft of an alternative embodiment implanted therein, such as to treat an aneurysm within the lumen.
Figure 6:
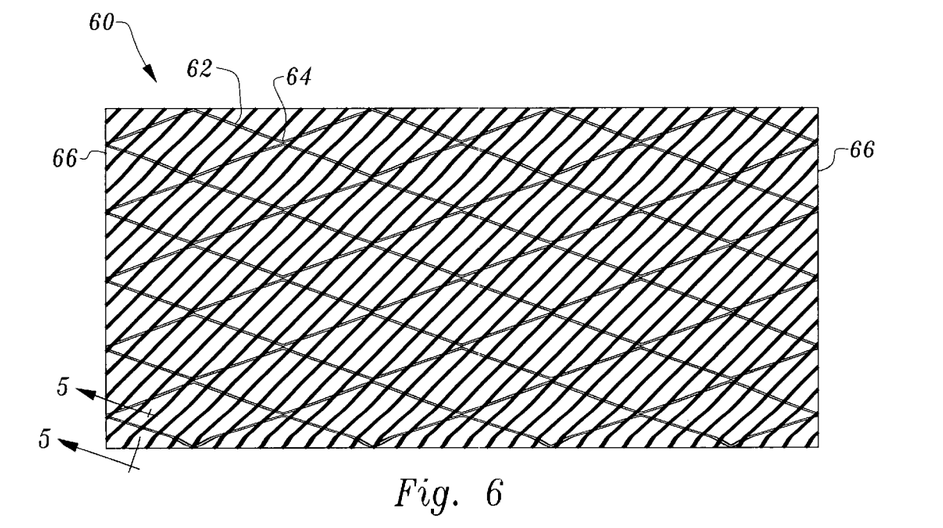
FIG. 6 is a cylindrical projection of a second alternative stent-graft configuration featuring flat edges.

With particular reference to FIGS. 4 and 6, details of two variations on the preferred embodiment are described. FIG. 4 depicts an implanted stent 50 within a body lumen L which has an aneurysm X therein with a neck N adjacent the body lumen L. The implanted stent 50 is radially expanded within the lumen L adjacent the aneurysm X so that fluid flow passes through the interior of the implanted stent 50 rather than accessing the aneurysm X.

With particular reference to FIG. 6, a flat edge stent 60 is shown. The flat edge stent 60 has a configuration similar to the implanted stent 50 of FIG. 4. However, the flat edge stent 60 exhibits flat edges 66 rather than angled edge facets of the implanted stent 50 of FIG. 4. These variations between the implanted stent 50 and the flat edge stent 60 merely illustrate two of an infinite variety of minor modifications to the stent-grafts 10 of the preferred embodiment according to this invention.

With the flat edge stent 60, segments 62 extend between the joints 64 in a somewhat diamond pattern. A film is continuous and surrounds each of the segments 62 and joints 64. For such a stent-graft 60 configuration, the film would need sufficient flexibility to accommodate the distortion which would accompany radial expansion of such a stent. If the stent is implanted with a direct surgical technique radial expansion is not necessary, overcoming the need to selectively attach the film to the underlying support structure only at selected locations as described in detail above.

Figures 7, 9:
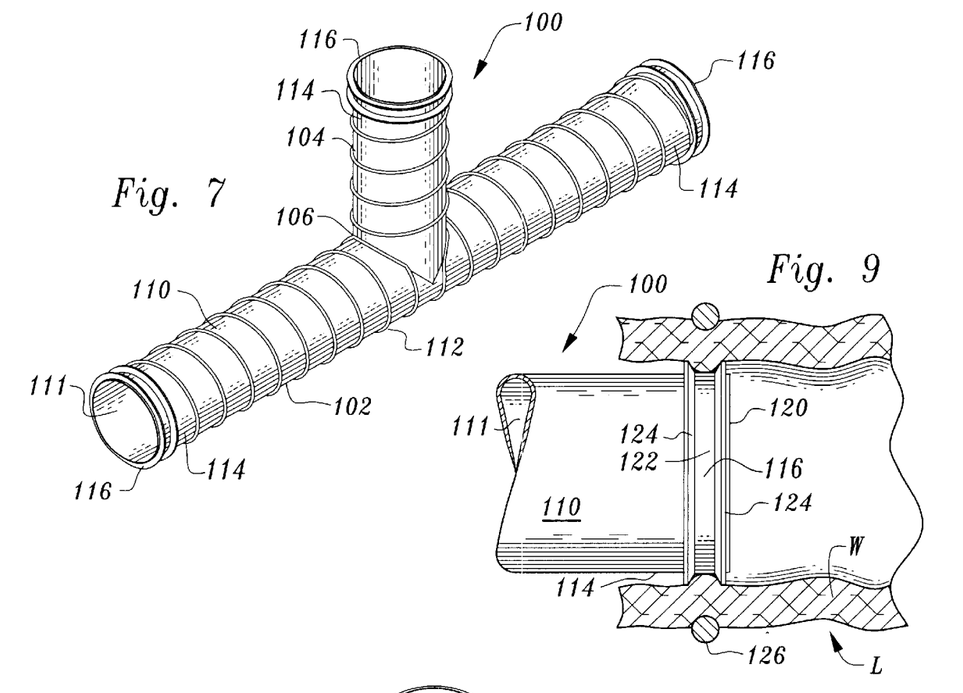
FIG. 7 is a perspective view of a stent-graft having a T-shape and with a spiral support structure external to a support layer which includes both a main arm and a side arm of the T-structure.
FIG. 9 is a sectional view of a body lumen illustrating a coupling system for ends of the stent-graft shown in FIG. 8.

With particular reference to FIGS. 7–13, details of a first primary alternative embodiment of the radially expandable stent-graft 10 of this invention is described. FIG. 7 depicts a T-shaped stent-graft 100 for implantation at a surgical site where a lumen L has diverging arms. The stent-graft 100 includes a main arm 102 and side arm 104 with an intersection 106 between the main arm 102 and the side arm 104. An exterior surface 110 is continuous between the main arm 102 and the side arm 104. An interior surface 111 is continuous between the main arm 102 and the side arm 104. A spiral support structure 112 is optionally provided adjacent the exterior surface 110 (FIG. 7).

Figures 8, 10:
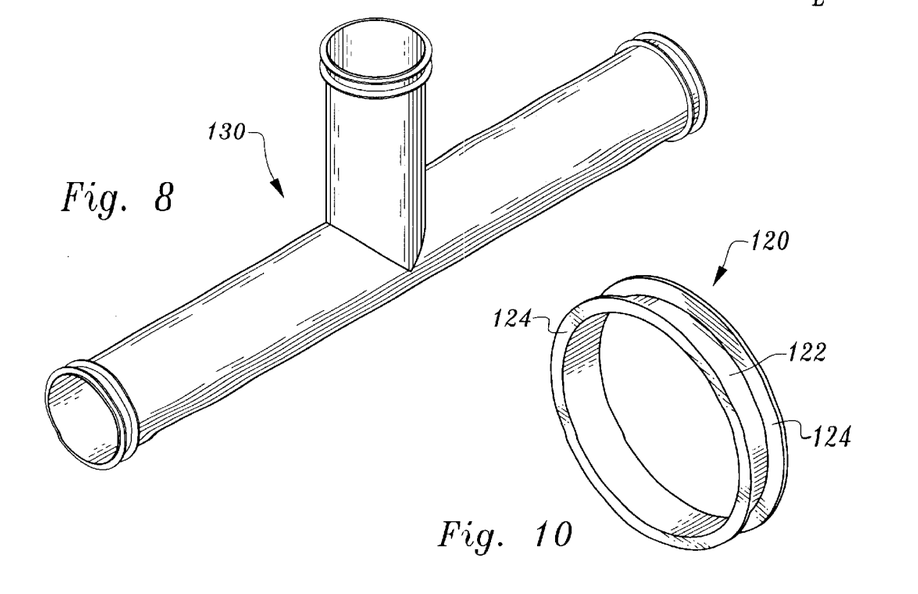
FIG. 8 is a perspective view of a stent-graft which does not include any support structure and which includes a collar of a coupling system for attachment of the stent-graft to a body lumen.
FIG. 10 is a perspective view of a collar portion of the coupling system shown in FIG. 9.

FIG. 8 depicts a stent-graft 130 which is a slight variation on the stent-graft 100 which does not include this spiral support structure 112. Ends of the stent-graft 100 include tips 114 with couplings 116 adjacent thereto. Each coupling 116 includes a collar 120 with a circumferential groove 122 located between two flanges 124 (FIG. 10). A band 126 (FIG. 9) is sized to reside within the groove 122 with portions of the wall W of the lumen L trapped between the groove 122 and the collar 120 and the band 126. This coupling 116 system is merely one form of system for securely attaching ends of the stent-graft 100 or other stent-grafts of this invention to body lumens L. The collar 120 is preferably attached to the tube structure of the T-graft 100 or other stent-graft by having the collar 120 embedded between layers of film, such as the layers 42, 44 of the film 40 of the preferred embodiment.

When the stent-graft 100 or stent-graft 130 is utilized direct surgical implantation is contemplated rather than intraluminal implantation. However, some combination of both radially expandable stent-graft 10 and T-shaped stent-graft 100 configurations could be combined together. The stent-graft 100 has its exterior surface 110 and interior surface 111 formed in a manner similar to that forming the film 40 of the stent-graft 10 of the preferred embodiment. Specifically, the parylene film is preferably utilized to form the surfaces of the stent-graft 100. A thickness of the parylene film can be enhanced so that the stent-graft 100 can be provided with the strength characteristics required, both with and without additional cylindrical or other support structure.

Figures 11, 12, 13:
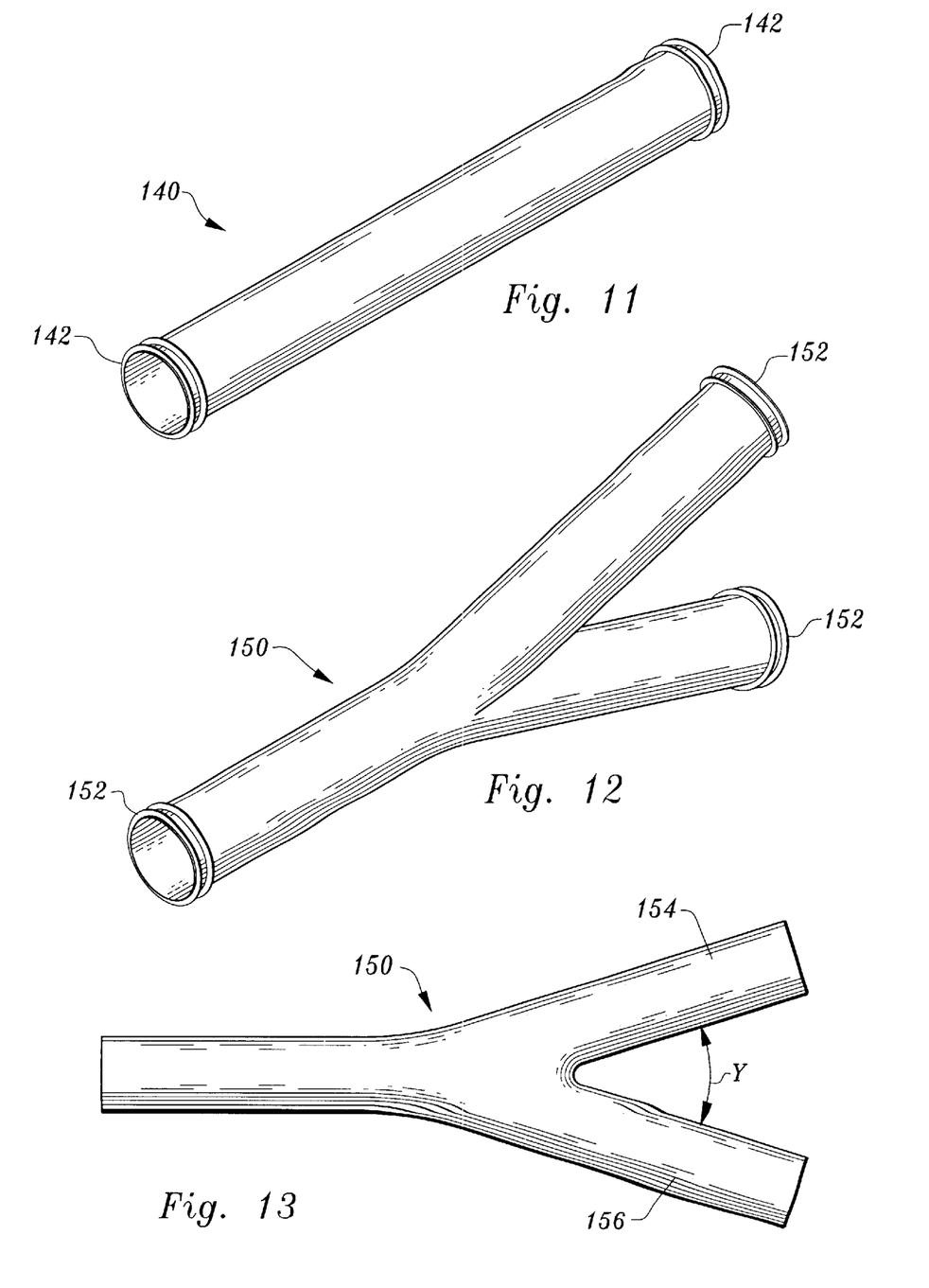
FIG. 11 is a perspective view of a stent-graft having a plain cylindrical configuration with collars of coupling systems located adjacent ends of the stent-graft and with no support structure.
FIG. 12 is a perspective view of a divergent stent-graft without any support structure and with portions of coupling systems adjacent various ends of the arms of the divergent stent-graft.
FIG. 13 is a top plan view of that which is shown in FIG. 12.

FIG. 11 shows a linear stent-graft 140 with tip collars 142 thereon similar to the collar 120 of FIG. 10. The linear stent-graft 140 is entirely formed from parylene film and provides a simplest form of this invention. FIG. 12 depicts a divergent stent-graft 150 with tip collars 152 similar to the collar 120 of FIG. 10. The divergent graft 152 would be utilized to replace body lumens L which include a divergent pathway. FIG. 13 provides a top plan view of the divergent stent-graft 150. A diverging angle Y defines an amount that the two diverging arms 154, 156 extend away from each other and would preferably match an angle of the lumen being replaced.

Figures 14, 15, 16:
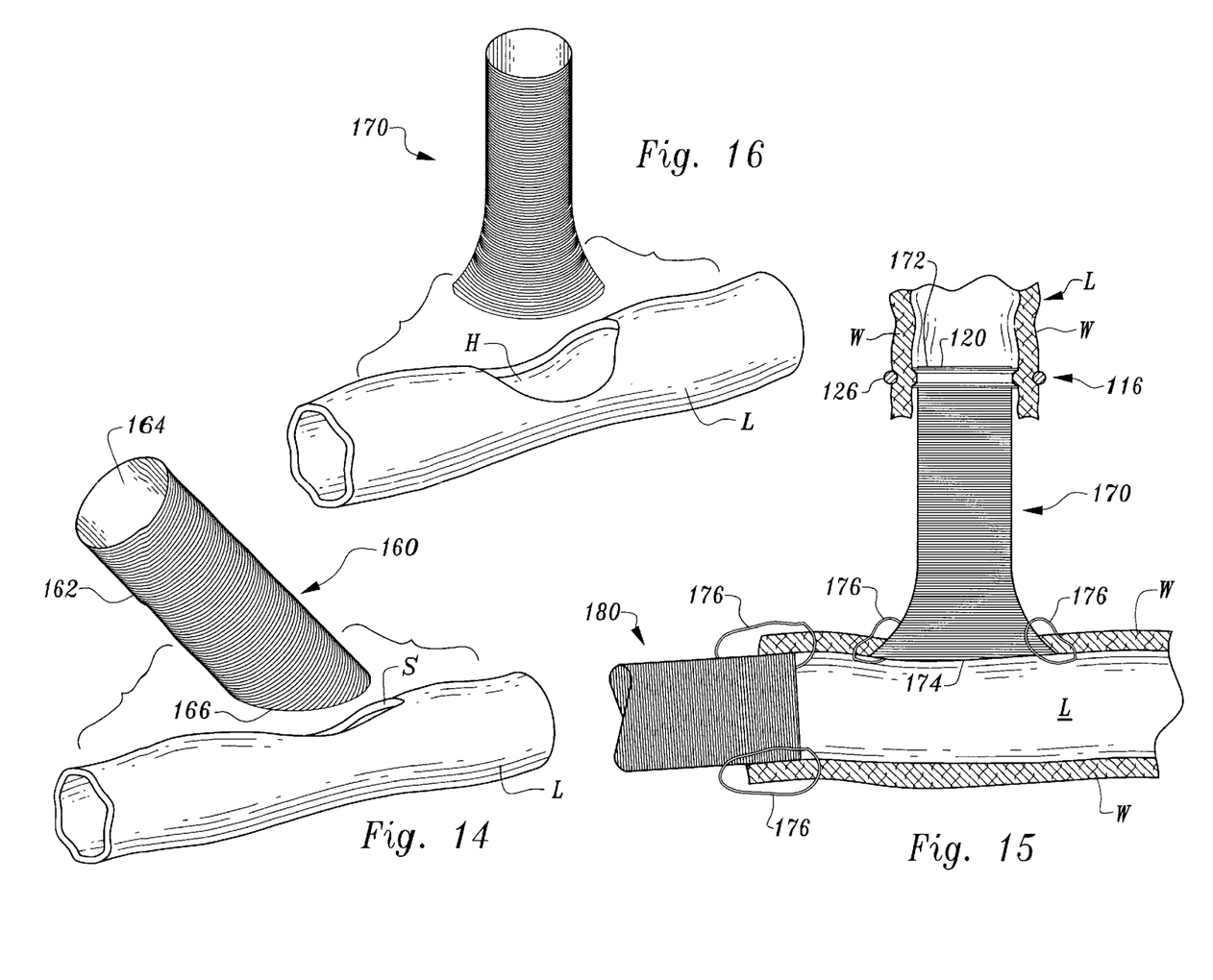
FIG. 14 is a perspective view of a lumen and stent-graft combination with the stent-graft including a woven fabric therein and shown during coupling to a slit in the body lumen.
FIG. 15 is a sectional view of a flared stent-graft and a body lumen with a flared end of the stent-graft attached to a hole in the body lumen with sutures.
FIG. 16 is a perspective view of that which is shown in FIG. 15 immediately before attachment of the stent-graft to the body lumen with the sutures.

With particular reference to FIGS. 14–16, details of a second alternative embodiment of this invention are described. Particularly where suturing is to be utilized, it is desirable that a woven mesh or wound support structure 162 be included so that a stent-graft is provided such as the fabric angled stent-graft 160 (FIG. 14), the flared graft 170 (FIGS. 15 and 16) or the cylindrical graft 180 (FIG. 16, left side). The cylindrical graft 180 is particularly useful to replace or reinforce a section of a body lumen L by placement in-line with the body lumen L and attached at both ends with sutures 176 and/or couplings 116 to portions of the wall W of the lumen L adjacent the damaged portion of the lumen L. Other support structures of a fabric or a metallic nature could similarly be utilized, with the term "support structure" defining any structure coupled to the film 40 which is provided to give greater strength to the film 40. Such a woven wound or mesh fabric support structure 162 could be coupled to a parylene film in a manner similar to that described in the placement of the cylindrical support structure 18 onto the film 40 of the stent-graft 10 of the preferred embodiment.

Alternatively, the fabric angled stent-graft 160, flared stent-graft 170 or cylindrical graft 180 can include both a structure similar to the cylindrical support structure 18 of the preferred embodiment and the woven support structure 162 so that both physical structural support and support for suturing can be provided along with the film provided by the parylene film.

With particular reference to FIG. 14, a slit S is formed in the wall of the lumen L and a beveled end 166 opposite a flat end 164 of the fabric angled graft 160 is inserted into the slit S. Sutures 176 (FIG. 15) could then be utilized to secure the beveled end 166 of the fabric angled stent-graft 160 to the lumen L. Because the fabric angled stent-graft 160 includes both the woven fabric support structure 162 and the film, the stent-graft 160 can securely hold the sutures 176 with the film holding the woven fabric support structure 162 together adjacent the sutures 176 so that leakage and tearing are resisted.

As an alternative, a hole H can be formed in the lumen L and a flared stent-graft 170 can be provided with a cylindrical edge 172 and a flared end 174. Sutures 176 would be utilized between the flared end 174 and the wall W of the lumen L to secure the flared stent-graft 170 to the lumen L. FIG. 15 illustrates how a combination of the coupling system 116 including the collar 120 and the band 126 can be utilized together with sutures 176 within a single flared stent-graft 170. Numerous other combinations of the concepts disclosed herein can similarly be combined. For instance, a combination of couplings 116 and sutures 176 could be utilized at a common end of a stent-graft.

Sutures 176 can be utilized on both flared ends 176 and non-flared ends of other stent-grafts. A woven fabric support structure 162 can be provided within any of the stent-grafts disclosed in this invention. Similarly, cylindrical support structure 18, such as that disclosed in FIGS. 1 and 2, can be incorporated into the film of the various different stent-grafts disclosed herein. Also, a variety of different stent-grafts can be provided with a variety of different arm configurations with varying different diverging angles to provide the geometric configuration desired for proper fluid flow therethrough.

Should a stent-graft be desired which includes both a cylindrical support structure 18 like that of the stent-graft 10 of the preferred embodiment and a woven fabric support structure 162 such as that depicted in FIGS. 14–16, the following forming process can be followed. As described in detail above, a first inside layer 42 could initially be formed upon a mandrel. A woven mesh or wound fabric support structure 162 could then be placed adjacent a side of this first inside layer 42 opposite the inside surface 43. A second middle layer can then be deposited within the vacuum chamber to secure the woven fabric support structure 162 to the first inside layer 42. Finally, the cylindrical support structure 18 can optionally be placed upon the second deposited middle layer and appropriately masked as necessary to facilitate radial expansion without distortion or damage to the film. A third and final outside layer is then deposited upon the cylindrical support structure 18. Finally, the masking agent is removed. The second and third layers could conceivably also be deposited simultaneously as a single final layer over the woven fabric support structure 162 and the cylindrical support structure 18.

The mandrel can then be removed using a variety of different techniques. If the stent-graft is linear such as the stent-graft 140 (FIG. 11) or cylindrical graft 180 (FIG. 15). The mandrel can conceivably be forced out of the linear stent-graft 140 or the linear stent-graft 140 can be provided with a sufficient slight taper so that the mandrel can easily be removed. Where T-shaped stent-grafts 100 or divergent stent-grafts 150 are utilized, a two-piece mandrel can be utilized. Alternatively, the mandrel can be formed from a material which is dissolvable so that the mandrel can be dissolved, such as dissolving a metallic mandrel with an appropriate dissolving agent.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When structures are identified as a means to perform a function, the identification is intended to include all structures which can perform the function specified.

What is claimed is:

1. A method for forming a stent-graft for implantation into a body lumen, the stent-graft having an elongate tube structure with at least two open ends, the tube structure including a film of solid material, the film having an inside surface facing a central axis and an outside surface facing away from the central axis, the method including the steps of:

providing a mandrel with an external surface matching a desired contour for the inside surface of the film of the tube structure;

placing the mandrel in a vacuum chamber with a vacuum sufficient to facilitate vapor deposition;

depositing a first layer of the film onto the mandrel to form the tube structure; and removing the mandrel from inside the film.

2. The method of claim 1 wherein said removing step includes the step of dissolving the mandrel.

3. The method of claim 2 wherein said providing step includes providing a mandrel formed from a metallic material, and wherein said removing step includes the step of chemically dissolving the metallic mandrel from within the tube structure.

4. The method of claim 1 including the further steps of:

locating a support structure over the first layer of film establishing the tube structure in said depositing step, the support structure formed from a material different than the first layer of the film forming the tube structure; and additionally depositing a second layer of the film material onto the support structure and the first layer of film establishing the tube structure in said depositing step to at least partially embed the support structure within the first and second layers of film material forming the tube structure.

5. The method of claim 4 wherein said additionally depositing step is preceded by the step of masking portions of the support structure at which deposition of the second layer of film material is not desired, such that the support structure is selectively partially embedded within the tube structure during said additionally depositing step.

6. The method of claim 1 including the further steps of:

positioning a collar adjacent at least one of the ends of the tube structure after said depositing step; and additionally depositing surface layer material onto the tube structure and the collar, said collar including a groove extending circumferentially between two flanges.

7. A method for forming a radially expandable stent-graft for implantation into a body lumen, the stent-graft having an elongate tube structure including at least two open ends, the tube structure including a film of solid material, the film having an inside surface facing a central axis and an outside surface facing away from the central axis, the method including the steps of:

providing a mandrel with an external surface matching a desired contour for the inside surface of the film of the tube structure;

placing the mandrel in a vacuum chamber;

depositing by vapor deposition a first layer of the film material onto the mandrel to form the tube structure;

orienting a radially expandable support structure formed from a material distinct from the film material adjacent a side of said first layer of said film material opposite the mandrel;

putting a masking agent over areas on the radially expandable support structure that move in directions other than purely radially when the radially expandable support structure is radially expanding;

additionally depositing a second layer of the film material onto the radially expandable support structure and the tube structure;

removing the masking agent so that the radially expandable support structure is only embedded within the tube structure at locations where the masking agent was not provided; and removing the mandrel.

8. The method of claim 7 including the further steps of:

locating a woven support structure over said tube structure formed in said depositing step; and additionally depositing a supplemental layer of the film material onto the woven support structure and the tube structure to at least partially embed the woven support structure within the layers of the film forming the tube structure.

9. A method for forming a stent-graft for implantation into a body lumen, the stent-graft having an elongate tube structure with at least two open ends, the tube structure including a film of solid material, the film having an inside surface facing a central axis and an outside surface facing away from the central axis, the method including the steps of:

providing a mandrel with an external surface matching a desired contour for the inside surface of the film of the tube structure such that the film is non-porous;

placing the mandrel in a vacuum chamber;

depositing a first layer of the film onto the mandrel to form the tube structure; and removing the mandrel from inside the film.

10. A method for forming a stent-graft for implantation into a body lumen, the stent-graft having an elongate tube structure with at least two open ends, the tube structure including a film of solid material, the film having an inside surface facing a central axis and an outside surface facing away from the central axis, the method including the steps of:

providing a mandrel with an external surface matching a desired contour for the inside surface of the film of the tube structure;

placing the mandrel in a vacuum chamber;

depositing by vapor deposition a first layer of the film onto the mandrel to form the tube structure; and removing the mandrel from inside the film.

11. A method for forming a stent-graft for implantation into a body lumen, the stent-graft having an elongate tube structure with at least two open ends, the tube structure including a film of solid material, the film having an inside surface facing a central axis and an outside surface facing away from the central axis, the method including the steps of:

providing a mandrel with an external surface matching a desired contour for the inside surface of the film of the tube structure;

placing the mandrel in a vacuum chamber;

depositing a first layer of the film onto the mandrel to form the tube structure; and removing the mandrel from inside the film.

* * * * *